United States Patent [19]

King et al.

[11] Patent Number: 5,243,407

[45] Date of Patent: Sep. 7, 1993

[54] ON-LINE PAPER SHEET FORMATION CHARACTERIZING METHOD AND DEVICE

[75] Inventors: Harriss King, Cupertino; Lee M. Chase, Los Gatos; Leonard M. Anderson, San Jose, all of Calif.

[73] Assignee: Measurex Corporation, Cupertino, Calif.

[21] Appl. No.: 674,432

[22] Filed: Mar. 22, 1991

Related U.S. Application Data

[63] Continuation of Ser. No. 243,321, Sep. 9, 1988, abandoned, which is a continuation-in-part of Ser. No. 930,142, Nov. 12, 1986, Pat. No. 5,092,678.

[51] Int. Cl.⁵ ............................................. G01N 21/86
[52] U.S. Cl. .................................... 356/429; 250/571
[58] Field of Search ................. 356/429; 250/559, 571

[56] References Cited

U.S. PATENT DOCUMENTS

| | | |
|---|---|---|
| 3,114,791 | 12/1963 | Zabell . |
| 3,135,819 | 6/1964 | Quinn . |
| 3,228,282 | 1/1966 | Barker . |
| 3,325,649 | 6/1967 | Bird . |
| 3,458,261 | 7/1969 | Bentley . |
| 3,469,104 | 9/1969 | Hector . |
| 3,525,871 | 8/1970 | Lehtinen ............................ 356/430 |
| 3,824,021 | 7/1974 | Axelrod et al. . |
| 3,900,265 | 8/1975 | Merlen . |
| 4,019,066 | 4/1977 | Lucas et al. ........................ 356/429 |
| 4,288,160 | 9/1981 | Lodzinski . |
| 4,453,404 | 6/1984 | Powell . |
| 4,455,090 | 6/1984 | Roberts . |
| 4,644,174 | 2/1987 | Ouellette et al. .................. 250/572 |
| 4,648,712 | 3/1987 | Brenholdt ......................... 250/571 |
| 4,767,935 | 8/1988 | Anderson et al. ................. 250/571 |
| 4,770,538 | 9/1988 | Orkosalo . |

FOREIGN PATENT DOCUMENTS

| | | |
|---|---|---|
| 0311518 | 5/1988 | European Pat. Off. . |
| 868977 | 7/1949 | Fed. Rep. of Germany . |
| 1573647 | 8/1965 | Fed. Rep. of Germany . |
| 133467 | 1/1979 | Fed. Rep. of Germany . |
| 2147413A | 5/1985 | United Kingdom . |
| 2170905A | 2/1986 | United Kingdom . |

OTHER PUBLICATIONS

Article entitled "Specific Perimeter-A Graininess Parameter For Formation And Print-Mottle Textures" by Jordan et al. Pulp and Paper Research Institute of Canada, Jul. 1984.

Norman and Wahren Article entitled "Using a beta radiographic method", Svensk paper stidning No. 11 (1974) no month. pp. 397-406.

Norman and Wahren article entitled "Mass Distribution and Sheet Properties of Paper" Transactions of the Symposium held at Cambridge: Sep. 1973, pp. 7-73.

Undated M/K Systems Inc. advertisement.

Sep. 19, 1986 Pulp and Paper Monthly article re the Lippke formation sensor.

Primary Examiner—Richard A. Rosenberger
Attorney, Agent, or Firm—Spensley Horn Jubas & Lubitz

[57] ABSTRACT

A device for characterizing the formation of a sheet material is described. The device comprises a formation sensor for measuring the basis weight of the sheet material as the material passes through the sensor, and signal processing circuitry which receives a basis weight signal from the formation sensor and which produces three types of outputs, which outputs characterize: (1) the magnitude of variation in the sheet basis weight; (2) the strength of the weakest portion or portions of the sheet; and (3) the size of the flocs comprising the sheet. The formation sensor includes a light pipe that is held against the sheet as the sheet moves through the sensor, and that directs a small spot of light transmitted through the sheet to a light detecting device. The magnitude of small-scale variation in the sheet basis weight is computed by determining the ratio between average value of the basis weight signal and the varying or AC component of the basis weight signal.

13 Claims, 3 Drawing Sheets

ON-LINE PAPER SHEET FORMATION CHARACTERIZING METHOD AND DEVICE

CROSS-REFERENCE TO RELATED APPLICATIONS

This is a continuation of application Ser. No. 07/243,321, filed Sep. 9, 1988, now abandoned, which is a continuation-in-part of application Ser. No. 06/930,142, filed Nov. 12, 1986, now U.S. Pat. No. 5,092,678.

BACKGROUND OF THE INVENTION

1. Field of the Invention

This invention relates to a device and method for characterizing the quality of a sheet of paper, and more specifically, to a device and method which measure the distribution of cellulose fibers in a sheet of paper by monitoring the variations in the intensity of a narrow beam of light transmitted through the sheet as the sheet moves perpendicularly through the beam.

2. Description of the Related Art

Paper is produced from a suspension of fibers. These fibers are usually made of cellulose, derived mainly from wood and rags. The evenness of the distribution of these fibers in a sheet of paper is of paramount importance to the optical, mechanical and printing properties of the sheet. Therefore, one of the chief goals for a paper maker is to develop a paper making process and adjust the parameters of the process to achieve as even a "basis weight" or distribution of these fibers in the finished sheet material as possible. In the paper making art, the term "basis weight" refers to the weight of the paper-forming fibers per unit area of the sheet surface. When the fibers are distributed evenly and the paper has a uniform basis weight, the sheet of paper will have its greatest strength, will look and feel smooth, and will be receptive to sharply defined lines of print. Conversely, local variations in the basis weight will yield a sheet having poor strength. This is because stress is concentrated in the areas of the sheet having fewer fibers, so that these areas of the sheet tear first. Furthermore, sheets having uneven basis weight may look and feel rough and will blur printed lines.

To characterize the quality of a sheet of paper, paper makers refer to the "formation" of the sheet. There is, apparently, no standard definition of "formation." However, for the present purpose "formation" will be defined as the manner in which fibers forming a paper sheet are distributed, disposed and intermixed within the sheet. In all paper sheets, the sheet-forming fibers are, at least to a certain extent, unevenly distributed in bunches called "flocs." However, sheets of paper having generally evenly distributed, intertwined fibers are said to have good formation. Conversely, when the fibers forming the sheet are unacceptably unevenly distributed in flocs, the paper sheet is grainy rather than uniform and is said to have poor formation.

A variety of devices exist for measuring various characteristics of the formation of paper sheets. In one such device, called a basis weight sensor (or microdensitometer), a beam of light is transmitted through the sheet as the sheet passes perpendicularly through the beam. The intensity of the beam is measured by a light detector after the beam is transmitted through the paper sheet. This light detector is positioned on the opposite side of the sheet from the light source. The light detector produces an electrical signal indicative of the intensity of the transmitted beam. As the basis weight of the portion of sheet through which the light beam is passing increases, the intensity of the beam transmitted through the sheet decreases. Thus, the electrical signal from the light detector is indicative of the basis weight of the sheet. In this type of basis weight sensor, the "light source" may be a source of visible light or alternatively may be some other type of radiation, as a beta ray device. That is, a variety of source/detector combinations may be used as long as the detector can sense the amount of radiation passing through the paper.

As previously mentioned, the fibers forming every sheet of paper tend to congregate in flocs. In any one sheet, these flocs will have a variety of sizes. Thus, as the paper moves perpendicularly through the light beam, the electrical signal produced by the light detector will be modulated at a plurality of frequencies corresponding to the distribution of floc sizes and also to the speed with which the paper sheet moves through the light beam. As the sheet speed increases, the frequency with which the flocs modulate the electrical basis weight signal increases. Similarly, smaller flocs modulate the signal at higher frequencies than larger flocs. The amplitude of these modulations corresponds to the local variations in basis weight or, what amounts to the same thing, the local variations in the distribution of the fibers forming the flocs.

In one technique, the formation characterizing device displays the average peak-to-peak variation in the electrical signal produced by a basis weight sensor. The average peak-to-peak value of the electrical signal is said to indicate the magnitude of variations in the basis weight of the sheet. However, for the reasons discussed below, this technique may give a false indication of the sheet formation.

In many instances, the paper maker will want to make a sheet having as even a fiber distribution as possible, i.e. one having good formation. To accomplish this, the paper maker will want to know, not only the magnitude of the variations in basis weight, but also the size distribution of the flocs. The paper maker will also want to know the strength of the lowest basis weight portions of the sheet. However, the previously described technique, which yields only the average peak-to-peak value of the basis weight signal, gives no indication of the size of the flocs creating these variations in the basis weight signal or the strength of the weakest areas of the sheet. Thus, this technique fails to completely characterize sheet formation.

In another technique for characterizing sheet formation, a beta radiograph is made of a sample sheet of paper. Light is then passed through or reflected off of the radiograph. Variations in the intensity of a narrow beam of this light are converted into an electrical signal as the radiograph moves, at a uniform speed, perpendicularly with respect to the beam. A graphical display is produced of the amplitude of the modulations of this electrical signal as a function of the wavelengths comprising the signal. This display is called a wavelength power spectrum. FIG. 1 illustrates one such display for several grades of paper having good, intermediate and poor formation. This technique has been discussed in great detail by Norman and Wahren in a number of papers, including their symposium paper "Mass Distribution and Sheet Properties of Paper".

For some commercial paper manufacturing situations, the Norman and Wahren technique may not be appropriate. First, as illustrated in FIG. 1, there is little difference between the wavelength power spectra of a well-formed sheet and a poorly-formed sheet at wavelengths below about 1 mm, whereas a considerable difference can be seen for wavelengths between about one millimeter and thirty-two millimeters. Thus, the Norman and Wahren technique produces more information than may be necessary for the paper maker to determine the formation of the sheet. Second, this technique provides so much information that its interpretation may be difficult for the non-expert: the paper maker may prefer a device and technique that provides him or her with only a few numbers, which together completely characterize the formation of the sheet, rather than an entire spectral display. Third, this technique, like the previously described technique for measuring the average peak-to-peak value of a basis weight signal, fails to provide the paper maker with an indication of the strength of the weakest portions of the sheet. Finally, this technique requires considerable time for the analysis of a given paper sample, and is restricted to "off-line" analysis — i.e., to samples which have been removed from the paper machine — whereas the paper maker may prefer to have an "on-line" device capable of rapidly analyzing the formation of the paper as it is actually being produced on the machine.

SUMMARY OF THE INVENTION

The present invention is directed to a method and device which provide a set of electrical output signals indicative of the following sheet formation parameters: (1) the magnitude of the variations in the basis weight of the sheet caused by flocs of predetermined minimum sizes or range of sizes; (2) the strength of the weakest portion or portions of the sheet; and (3) the size of the flocs forming the sheet. These output signals may be converted into numerical values and displayed to the paper mill operator. The operator can then use these numerical values to monitor the formation of the manufactured sheet and adjust the parameters of the paper making process to achieve a paper sheet having the desired characteristics. Alternatively, these electrical output signals can be fed into a computer or other device which would then use these output signals to automatically adjust the paper making process to achieve paper having the desired characteristics.

The device of the present invention includes a basis weight sensor for accurately measuring local variations in the basis weight of a sheet of paper. The sensor includes a light beam source, which is disposed on one side of the sheet, and a "receiver", disposed on the other side of the sheet opposing the light beam source. The receiver includes a light pipe, such as a narrow sapphire rod. One end of the rod abuts against the sheet on the opposite side of the sheet from the light source. As the sheet passes through the sensor perpendicular to the light beam, the sheet is held against the end of the rod so that only light which passes through the sheet can enter the rod. This rod directs at least a portion of the light beam to a light detecting device such as a photodiode. The photodiode then produces an electrical output proportional to the intensity of the light beam after the beam is transmitted through the sheet.

For purposes of this application for patent, a basis weight sensor detecting small scale variations in basis weight, as discussed in the preceding paragraph, will be referred to as a formation sensor. Other types of basis weight sensors, such as those utilizing a beta ray source and a beta ray sensitive receiver typically used for measuring large scale variations in basis weight, will simply be referred to as basis weight sensors.

As the sheet of paper passes through the formation sensor, local variations in the basis weight of the sheet create variations in the intensity of the light beam transmitted through the sheet. The light detecting device in the receiver portion of the sensor produces an electrical signal proportional to the intensity of the transmitted beam and hence inversely related to the basis weight of the portion of the sheet through which the detected portion of the beam is passing. Because paper consists of flocs of a variety of sizes, the electrical signal from the sensor is modulated at a number of frequencies as the paper sheet passes between the light source and receiver halves of the sensor. These frequencies are dependent upon both the speed with which the paper passes through the sensor and the size of the various flocs forming the sheet. That is, for a given paper speed, floc sizes of increasing size will modulate the basis weight signal at decreasing frequencies. Since the signal processing circuits of the present invention account for changes in the speed with which the paper passes through the sensor, the output signals characterizing formation are independent of the paper speed.

The signal processing circuitry of the present invention simultaneously subjects the basis weight signal to two different analysis channels. A first channel includes a further plurality of electrical channels. Each of these electrical channels processes basis weight signals from the formation sensor corresponding to a different predetermined range of floc size. Each succeeding channel corresponds to a floc size range for flocs of increasing size. This is accomplished by placing a bandpass filter at the input end of each channel. The signal from the formation sensor is fed into each of these bandpass filters. The bandpass filter of each succeeding channel has a frequency band with a high frequency cutoff approximately equal to the low frequency cutoff of the bandpass filter in the preceding channel. In addition, the frequency band for each of these bandpass filters is variable and is controlled to be proportional to the speed with which the paper passes through the sensor. Thus, the frequency band for the bandpass filter of each channel corresponds to flocs of a particular predetermined size range and continues to correspond to flocs of this predetermined size range even when the speed with which the paper moves through the sensor is changed.

The output of each bandpass filter is directed to a separate AC to DC converting circuit which converts the filtered signal from the associated bandpass filter to a steady, or DC, output proportional to the root-mean-square (hereinafter "RMS") value of the signal from the bandpass filter. The output of each AC to DC converter therefore indicates the magnitude of the variations in the basis weight of the sheet created by flocs of a certain size range (i.e. the flocs modulating the basis weight signal at a given frequency band).

The electrical signal from the formation sensor is also subjected to a second analysis channel for processing that produces an average value, or "DC" component, of the basis weight signal. The DC component signal is used for "normalization" of the signal and provides sensor calibration of output, as described further below. Normalization is accomplished by dividing the RMS value of the AC component for each bandpass filter by the DC component signal. The division is accomplished either by a hardwired divide circuit or in software.

Additionally, the signal from the formation sensor can be directed to a peak detector circuit. This circuit can be made to indicate the maximum intensity of the basis weight signal over a predetermined length of paper which passes through the formation sensor or the average of several signal peaks. A more intense transmitted light beam corresponds to a lower basis weight. Therefore, when the peak detector is made to indicate the maximum intensity of the basis weight signal, the magnitude of the output of the peak detector circuit characterizes the strength of the weakest point of the sheet. Alternatively, when the peak detector circuit is made to indicate the average of several signal peaks, then the output of this circuit characterizes an average of the strengths of several of the weakest points in the sheet.

Moreover, the signal from the formation sensor can also be directed to a floc size measuring circuit. The floc size measuring circuit includes a comparator circuit which compares the value of the signal from the formation sensor to a value indicative of the average basis weight of the sheet. The output from the comparator circuit indicates the rate at which the signal achieves a value corresponding to the average basis weight of the sheet. If the signal only relatively rarely crosses the line corresponding to the average basis weight, then the sheet is composed of flocs of relatively large size. Alternatively, if the basis weight signal frequently crosses the average basis weight line, then the sheet is made of relatively small flocs. Thus, since the speed with which the paper sheet passes through the formation sensor is known, the floc size measuring circuit can be used to compute, from the sheet speed and the output from the comparator circuit, the size of the flocs forming the sheet.

Each of the three parameters discussed above — the magnitude of variation in the basis weight, the strength of the weakest portion or portions of the sheet, and the floc size — relate to the formation or evenness of distribution of the fibers comprising the paper sheet. Since, as previously mentioned, the formation of a sheet of paper is of paramount importance to its optical, mechanical, and printing properties, a paper maker can use the three types of electrical output signals of the present inventive device to help achieve an even distribution of fibers, and hence a well-formed paper sheet.

DETAILED DESCRIPTION OF THE PREFERRED EMBODIMENT

A. The Basis Weight Sensor

Figure 2:
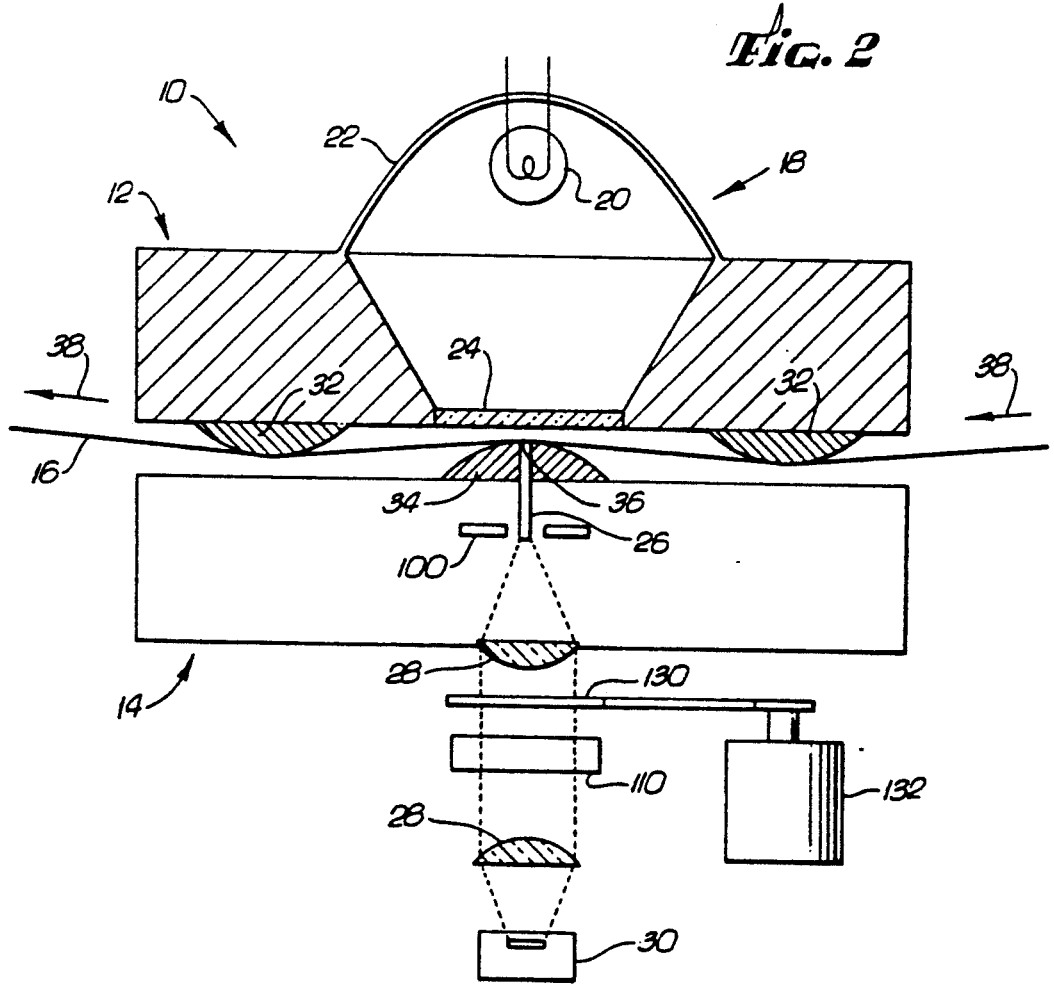
FIG. 2 illustrates one embodiment of the basis weight sensor of the present invention.

FIG. 2 illustrates a presently preferred embodiment of the basis weight sensor 10 of the present invention. Since the sensor 10 is used to measure the small-scale variation in basis weight, characterizing the sheet's formation, the sensor 10 will be referred to as a formation sensor. The sensor 10 can be considered as consisting of two halves, a "source" half 12 and a "receiver" half 14. The source half 12, disposed on one side of the sheet of paper 16, directs a beam of light through the sheet 16 whose formation is to be determined. The receiver half 14 is disposed on the opposite side of the sheet 16 and produces an electrical signal whose magnitude is proportional to the intensity of the light which is transmitted through the sheet 16. The source half 12 includes a light source 18, such as a high intensity incandescent lamp 20, and a reflector 22 for directing the beam of light from the lamp 20 toward the sheet 16. As the light travels toward the sheet 16, it passes through a diffuser 24 which randomizes the direction of the photons as the beam passes through it. It is important to use a diffuse source of light. If a non-diffuse source of light is used, the receiver half 14 of the formation sensor 10 may measure variations in the intensity of the transmitted beam caused by variations in the reflectance of the sheet surface to light coming from one particular direction, rather than variations in transmitted light intensity caused by local variations in basis weight of the sheet 16.

The receiver half 14 of the sensor 10 includes a 1 mm diameter sapphire light pipe 26 for directing a small spot of the diffuse light beam which is transmitted through the sheet 16 toward a lens system 28. This lens system 28 focuses the light from the light pipe 26 onto a light sensitive silicon photodiode 30. The photodiode 30 produces an electrical output signal proportional to the intensity of the spot of transmitted light.

It is important that the sheet 16 be held firmly against the end of the light pipe 36 as the sheet passes through the sensor 10 so that any light impinging upon the end of the light pipe 36 must have traveled through the sheet 16. To accomplish this goal, the source half 12 of the formation sensor 10 is formed with protrusions 32, called "skid plates", on opposite sides of the light pipe 26. In addition, the end of the light pipe 36 extends toward the sheet 16 and is protected by another skid plate 34 surrounding the light pipe 26 such that the paper sheet 16, travelling in the direction of the arrows 38 between the source and receiver halves of the sensor 10, is held by the skid plates 32, 34 against the end of the light pipe 36.

As the paper sheet 16 passes between and rubs against the skid plates 32, 34 and the end of the light pipe 36, the paper will tend to wear away the skid plates and the end of the light pipe 36. The skid plates 32, 34 are therefore constructed of an abrasion resistant material such as steel alloys or sapphire and the light pipe 26 is made of sapphire or some other similarly transparent but abrasion-resistant material.

B. The Signal Processing Circuitry

As previously mentioned, the formation sensor 10 produces an electrical signal whose magnitude is inversely related to the basis weight of the portion of the sheet 16 through which the detected spot of the light beam is transmitted. The sheet 16 is formed from flocs so that the transmitted beam intensity, and hence the sensor signal, varies as the paper sheet 16 passes through the sensor 10. The sensor signal is then amplified and the amplified sensor signal is fed to the signal processing circuitry. This circuitry is designed to process the sensor signal to yield electrical output signals indicative of: (1) the magnitude of the variations in basis weight of the sheet caused by flocs of a predetermined range of sizes; (2) the strength of the weakest portion or portions of the sheet; (3) the size of the flocs forming the sheet; and (4) the average value of the sensor signal.

Figure 4:
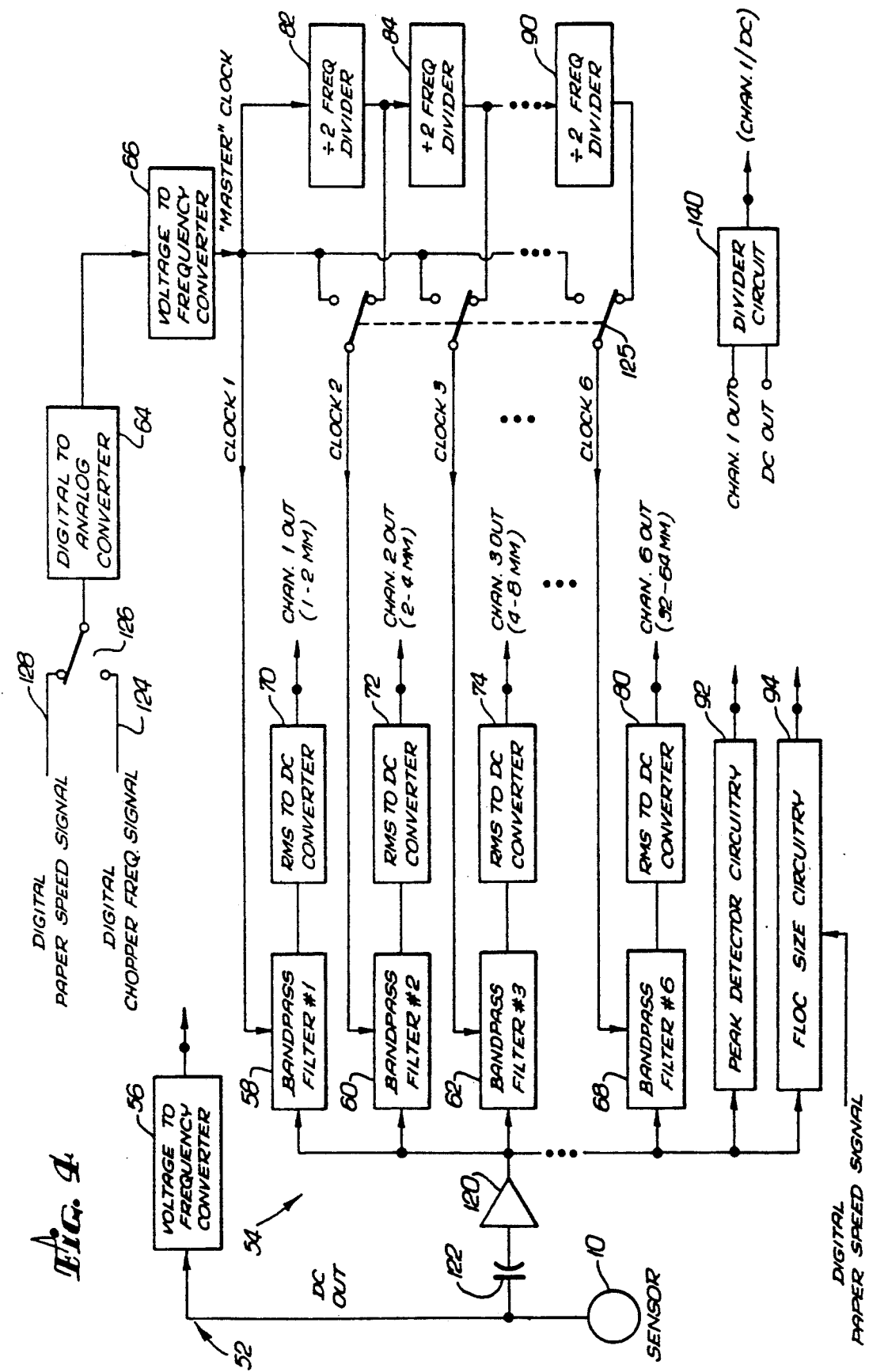
FIG. 4 illustrates a block diagram of one embodiment of the circuitry of the present invention used to process signals from the basis weight sensor of FIG. 2.

A presently preferred embodiment of the signal processing circuitry 50 is shown in block diagram form in FIG. 4. This signal processing circuitry 50 comprises two different analysis channels 52 and 54. In the first channel 52, the average value, or "DC" component, of the light intensity signal is obtained. In the second channel 54, the "AC" component of the signal, comprising the light intensity signal with the DC component removed, is obtained.

In order to obtain the DC component, preferably the light intensity signal from the formation sensor is fed directly to a voltage to frequency converter (VFC) 56. The VFC 56 puts out a digital pulse train whose frequency is proportional to the input voltage signal. By counting the pulses from the VFC for a fixed length of time, one obtains a count value that is proportional to the average voltage present at the input to the VFC during the time interval.

In order to obtain the AC component of the light intensity signal, the DC component is removed from the light intensity signal. The DC component may be conveniently removed by AC-coupling the basis weight signal by connecting the signal in series to a capacitor 122. The resulting AC component signal is amplified.

The signal processing circuitry of the present invention further comprises a plurality of bandpass filters 58-68 in the AC component analysis channel. Each bandpass filter 58-68 is associated with a particular electrical "channel". Each channel includes one of these bandpass filters 58-68 and an RMS-AC to DC converter 70-80.

The device of the present invention may have any number of channels. In the embodiment of FIG. 4, the device has six channels (channels 4-5 are omitted to simplify the figure). Each of the six bandpass filters 58-68 receives two input signals. The first input signal comes from the previously described formation sensor 10. This signal is directed to the first input of each bandpass filter 58-68. The second input of each bandpass filter is a "clock" input signal.

In the present preferred embodiment, each of the six bandpass filters 58-68 is an octave bandpass filter, in that basis weight signal components within a given frequency range of X through X/2 are passed unmodified, while frequency components outside this range are rejected. The high and low frequency cutoff values for a given bandpass filter are proportional to the frequency of its individual clock input signal. Under "on-sheet" operating conditions, the frequency of this clock input signal is not the same for each bandpass filter 58-68, but rather is set such that the high-frequency cutoff value of each filter is equal to the low-frequency cutoff value of the preceding filter. This causes the six filters to provide signal intensity information for six contiguous, non-overlapping frequency ranges, corresponding to six contiguous, non-overlapping floc size ranges.

To properly set the cutoff frequencies of the six bandpass filters under "on-sheet" operating conditions, a master clock frequency is fed to the second input of the first bandpass filter, comprising that filter's clock input signal. This clock frequency is then successively divided by 2 for each succeeding bandpass filter. Thus the bandpass range of each succeeding filter comprises frequencies that are smaller than those of the preceding filter by a factor of two. For example, if the master clock frequency M is set so as to provide a high-frequency cutoff value of X for the first filter 58, then the frequency range passed by the filter will be X through X/2. The clock frequency fed to the second filter 60 will be M/2, and thus the frequency range passed by the second filter will be X/2 through X/4. The clock frequency fed to the third filter 62 will be M/4, and thus the frequency range passed by the third filter will be X/4 through X/8. This pattern continues through all six filters, with the sixth filter having a clock input frequency of M/32 and a bandpass frequency range of X/32 through X/64. The frequency bandpass for each successive bandpass filter is thus correctly determined by utilizing a clock frequency which is half that of the preceding bandpass filter.

The formation sensor 10 cannot sense changes in basis weight that occur in less than 1 mm since the light pipe 26 (FIG. 2) of the sensor 10 has a 1 mm diameter. Thus, the highest frequency basis weight signal sent to the bandpass filters corresponds to 1 mm size flocs. Therefore, in the present embodiment, the master clock frequency of the signal sent to the second input of the first bandpass filter 58 is adjusted so that this filter 58 has a frequency band corresponding to variations in the basis weight caused by flocs of between 1 mm and 2 mm. The frequencies of the clock signals sent to the second inputs of the bandpass filters 60-68 of channels 2-6 are adjusted so that the frequency ranges of these bandpass filters correspond to floc size ranges of 2-4 mm, 4-8 mm, 8-16 mm, 16-32 mm, and 32-64 mm, respectively. The clock frequency of the second input to each bandpass filter 58-68 is also proportional to speed with which the paper passes through the sensor 10. Thus, the clock frequency of each bandpass filter continues to correspond to a basis weight signal frequency characteristic of flocs of the above-mentioned sizes, even when there is a change in the speed with which the paper sheet passes through the sensor 10.

In the present preferred embodiment, the second input signal to each bandpass filter 58-68 is derived by first measuring the speed with which the paper sheet passes through the sensor 10. Devices which measure the speed of a paper sheet are well known in the art. Many modern paper mills are highly automated and include a computer which monitors and controls various parameters of the paper making process. Thus, in the present preferred embodiment, a digital signal from the mill's computer indicative of the paper speed is conveniently used to control the second input, or the clock frequency, of the bandpass filter 58-68 for each channel. This digital speed signal is directed to a digital to analog converter 64 which receives the digital speed signal and outputs a voltage proportional to the paper speed. This voltage is then input to a voltage to frequency converter 66 (hereinafter "VFC"). The VFC 66 then outputs a signal having a frequency which is proportional to the output voltage of the digital to analog converter 64 and hence to the speed of the paper passing through the sensor 10.

The next step in deriving the second input signal is to obtain the high frequency cutoff value. Each channel, except the first channel, includes a frequency divider 82-90. The signal from the VFC 66 is fed directly into the second input of the first channel bandpass filter 58, and also into the frequency divider 82 of the second channel. The frequency divider 82 of the second channel divides the frequency of the signal received from the VFC 66 by two, and the resulting lower frequency signal is fed to the second input of the bandpass filter 60 of the second channel and also to the frequency divider 84 of the third channel. Thus, if the second input to the bandpass filter 58 of the first channel is at frequency M, which corresponds to the speed with which the paper passes through the sensor 10, then the frequency input to the bandpass filter 60 of the second channel is at frequency M/2. The signal output by the frequency divider 82 of the second channel is also fed as the input signal to the frequency divider 84 of the third channel. Each of the succeeding channels 4, 5, and 6 also have frequency dividers, for example frequency divider 90, which receives the signal from the frequency divider of the preceding channel and outputs a signal at one-half the frequency of the received signal. Thus, the output frequency of the third channel frequency divider 84 is at frequency M/4, which is fed to the third bandpass filter 62, the frequency of the signal fed to the fourth channel bandpass filter 64 is M/8, etc. The output of each channel's bandpass filter 58-68 is then processed to indicate the formation intensity of the sheet being sensed for floc sizes within the range covered by the particular channel.

To derive an output signal indicative of the magnitude of the variations in the basis weight of the sheet, the output of each bandpass filter 58-68 is directed to an associated AC to DC converter 70-80. Each AC to DC converter 70-80 produces a DC voltage equivalent to the RMS value of the AC signal output from the associated bandpass filter 58-68. The value of the DC voltage produced by each AC to DC converter 70-80 is proportional to the magnitude of variation in the basis weight signal caused by flocs of a particular size band. Since the frequency band of the bandpass filters 58-68 in each succeeding channel is set to succeedingly lower frequencies, the magnitude of the RMS to DC converter output voltage of each succeeding channel corresponds to the magnitude of variation in the basis weight of the sheet caused by succeedingly larger floc sizes. The device of the present invention provides the magnitude of the basis weight variations in the sheet caused by flocs in a particular size range.

Many standard "RMS" AC to DC converters actually measure the peak-to-peak voltage of the incoming signal and then provide an output DC signal which corresponds to the true RMS value of the input signal only if the input signal is sinusoidal. However, the basis weight signal waveshape is generally not sinusoidal. It is, therefore, usually important that the AC to DC converters 70-80 of the present invention output a DC voltage corresponding to the true RMS value of the basis weight signal. Otherwise, the output signal of these AC to DC converters 70-80 may provide an inaccurate measure of the basis weight variations.

The magnitude of the variations in the light transmission signal may be translated via a calibration procedure into the magnitude of actual basis weight variations in the sheet. This calibration is based on the following empirical relationship between basis weight and the transmitted light signal:

$$BW = A + B*ln(V)$$

where BW is the basis weight, V is the transmitted light signal, and A and B are constants which depend on the characteristics of the paper being manufactured (for example, its color, ash content, etc.). As previously noted, the "formation" of a sheet is actually the small scale variation of the basis weight. If the size of the basis weight variability is not extreme, the relationship between basis weight variability and transmitted light signal variability is (from the above equation):

$$RMS(BW) = B*RMS(V)/V$$

where RMS (BW) is the RMS variation in the basis weight, B is the slope of the BW vs. ln(V) curve, V is the average or DC component of the transmitted light signal, and RMS (V) is the RMS value of the AC component of the transmitted light signal. The RMS light variation value above can be either the total RMS variation in the light signal or the RMS variation in a given frequency band of the light signal. Furthermore, the signals from the various bandpass filters may be added statistically to obtain a total RMS value. This total RMS value is equal to the square root of the sum of the squares of the individual bandpass signals.

By the equation above, it can be seen that a division of the AC component of the transmitted light signal by the DC component is necessary. This can be done in a divider circuit 140, or the division can be carried out digitally by means of a computer monitoring the AC and DC signals. The constant B may be easily determined experimentally, as described below. The division or normalization of the AC signal components by the DC component, in addition to providing output values proportional to the true small-scale basis weight variability, also provides other advantages. Since the AC and DC components are simply different components of the same detected signal, extraneous factors affecting the overall signal strength will have no affect on the ratio of the AC and DC values. Thus, extraneous factors such as movement of the source lamp relative to the receiver light pipe, drifts in lamp intensity, dirt buildup on either the source or receiver light pipe, and overall electronic gain settings will have no effect on the ratio. The compensation for these effects will occur dynamically and does not depend on an off-sheet sensor standardization. In addition, since the absolute variation in basis weight is proportional to the relative variation in the transmitted light intensity signal, measuring the ratio of the RMS signal variation to the DC component signal will allow calibration of the sensor in terms of true basis weight units, rather than in an arbitrary scale.

The second parameter indicative of sheet formation, the strength of the weakest portion of the sheet, is obtained by feeding the sensor output to the input of a peak detecting circuit 92. The peak detecting circuit 92 may be designed to provide a DC output proportional to the maximum sensor signal in a predetermined time period or for a predetermined length of sheet passing through the sensor 10. The magnitude of this signal indicates the weakest point in the sheet. Alternatively, the peak detector circuit 92 may also be designed to produce an output proportional to the average of several signal peaks over a set period of time or length of sheet passing through the sensor 10. In this latter case, the output of the peak detector circuit 92 would characterize an average weak spot in the sheet.

The signal processing circuits 50 of the present invention may provide the paper manufacturer with yet a third output signal indicative of another characteristic of the paper sheet — the average floc size. To obtain this parameter, the sensor output is fed to a floc size measuring circuit 94. This circuit 94 counts the number of times, during a predetermined time interval, that the output signal achieves a value corresponding to the average basis weight of the sheet. The frequency with which this signal crosses this average basis weight value divided by the speed of the paper through the sensor indicates the average size of the flocs forming the sheet. The floc size measuring circuit 94 could electronically perform this division and output a signal corresponding to the average floc size, or the division could be carried out digitally by means of a computer monitoring the signal crossover rate. For example, if the paper sheet is moving at 1000 m/min and the output signal achieves a value corresponding to the average basis weight 1667 times in a one second time interval, then the average floc size of the sheet is 10 mm (1000 m/min*1 min/60 sec*1 sec/1667 crossings). Thus, by sensing the basis weight of the paper sheet along a line or curve (hereinafter collectively "line") along the sheet surface, the device and method of the present invention can provide the paper manufacturer with an output signal indicative of the size of the flocs forming the sheet.

C. Use and Calibration of the Device

In a paper mill, paper is typically produced in sheets about 25 feet wide. To characterize the entire sheet, one basis weight formation sensor can be moved or "scanned" back and forth in the "cross direction" of the sheet (i.e. across the width of the sheet) as the sheet moves along in the "machine direction" (i.e. the lengthwise direction). Alternatively, a plurality of sensors can be scanned back and forth in the cross direction across only a part of the width of the sheet. If, for example, 50 basis weight sensors are used on a 25 foot wide sheet, then each sensor would be made to scan back and forth across a 6 inch wide strip of the sheet. Typically, paper mills produce such sheets at more than 1000 feet per minute and the back and forth scanning speed of the sensor in the present embodiment may be set at 60 feet per minute. Thus, the cutoff frequencies of the bandpass filters may be made proportional only to the speed with which the sheet moves in the machine direction without introducing substantial error into the output readings. The additional contribution to the speed with which the paper moves through the sensor, caused by the cross directional movement of the sensor, is minimal, and can usually be ignored.

For the receiver part 14 of the basis weight formation sensor 10 (FIG. 2) to operate properly, the light from the source side 12 of the sensor must be aligned directly opposite the sheet from the receiver 14. However, the two halves of the sensor 10 cannot be directly connected together since the paper sheet 16 passes between these two halves. A number of different mechanisms can be used to keep the two halves of the sensor 10 directly opposite to each other as they scan back and forth across the sheet 16. One such device, for example, consists of two tracks (not shown), one on each side of the sheet 16. The source side of the sensor 12 rides on one of the tracks and the receiver side of the sensor 14 rides on the other track. A gear or pulley system moves the two halves of the sensor in unison and opposite each other back and forth across the width of the sheet 16. In this way, the source 12 and receiver 14 halves remain directly opposite each other without the necessity of penetrating the sheet with a connecting member.

Figure 1:
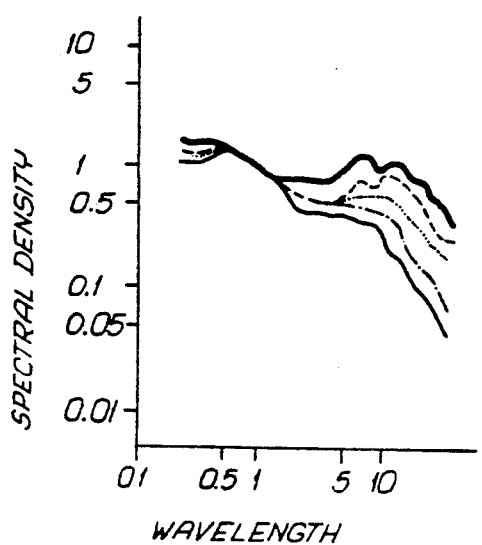
FIG. 1 illustrates wavelength power spectra for several different grades of paper.
Figure 3:
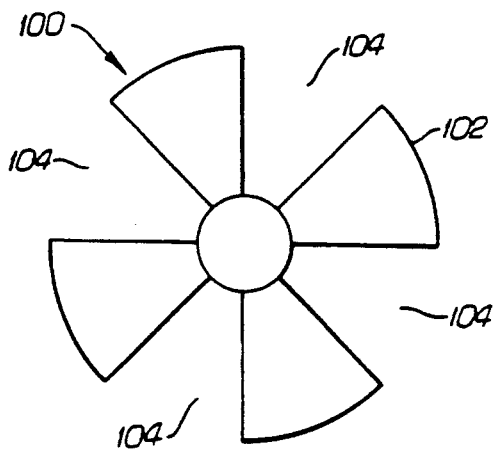
FIG. 3 illustrates a chopper wheel for calibrating the device of the present invention.

Standardization of the device of the present invention may be done "off sheet", i.e., with no paper sheet in place between the two sensor halves. If necessary, a neutral density filter 130 can be inserted by way of a pivot 132 in order to reduce the off sheet light to an appropriate level. To calibrate the outputs of the bandpass filters, a chopper wheel 100 (FIGS. 2-3) is positioned between the sensor's light source 18 and a photodiode 30. In the present embodiment, the chopper wheel 100 is positioned at the base of the light pipe 26 in the receiver 14. It could, with equal facility, be placed before the diffuser 24 in the source 12. The chopper wheel 100 is made from a circular disk 102 of opaque material having a plurality of radial slots 104 positioned around the wheel 100. The chopper wheel 100 is driven at a known rotational speed so that the photodiode 30 receives pulses of light. The pulsing rate is determined by the predetermined speed of rotation of the wheel 100.

For standardization, the clock circuitry in the AC signal analysis hardware illustrated in FIG. 4 can be switched such that all of the bandpass filters are fed the same clock frequency, shown in FIG. 4 as the digital chopper frequency signal 124. A switch 126 may be used to select between the chopper frequency signal 124 and the digital paper speed signal 128. When the chopper frequency signal is selected and a clock input selector switch 125 is activated (placed in the opposite position to that illustrated in FIG. 4), the bandpass filters all receive the same clock frequency, thereby setting the filters so that all are centered at the chopper pulse frequency. The output of the six bandpass channels will now all be proportional to the RMS value of the chopped light signal. This allows one to determine the electronic gains of the six AC channels relative to the DC channel (and to one another), as discussed below.

The chopper wheel is designed to completely block and then completely expose the light beam as the wheel turns. When completely exposed, the light intensity reaching the photodiode 30 is the same as what would be measured when the chopper is turned off and held stationary, out of the way of the beam. The RMS value of the chopped signal measured by the bandpass filters is proportional to this full intensity value, with an unchanging proportionality constant which can easily be measured experimentally. Thus, measuring the RMS value of the chopped signal with the AC channels, and the full intensity value of the unchopped signal with the DC channel, allows one to precisely determine the relative gain difference between each of the AC channels and the DC channel. The electronic gain of each AC channel may then be adjusted so as to have the same gain as the DC channel, or a correction for gain difference may be made by a computer monitoring the AC and DC signals. In this way, the chopper wheel allows the relative gains of the AC and DC channels to be equalized so that it is possible to determine an accurate ratio of the AC signal value to the DC signal value during on-sheet operation.

The above standardization procedure can be done periodically and automatically to ensure the continuing accuracy of the AC to DC gain ratio.

Other devices which modulate the intensity of the light reaching the light detector can be used in place of a chopper wheel 100. For example, a tuning fork, the arms of which oscillate into and out of the light beam at a known frequency, could be used in place of a chopper wheel 100.

Different types of paper will preferentially absorb or reflect certain frequencies of light. Therefore, to optimize the sensitivity of the basis weight sensor to changes in basis weight, an optical band pass filter 110 (FIG. 2) may be placed in the path of the light beam. This band pass filter 110 will preferentially pass light of certain frequencies to the photodiode 30.

As noted previously, the sensor of the current invention can be calibrated to provide an output equal to the true small scale basis weight variability in the sheet. This calibration requires a determination of the proportionality constant between the basis weight variability and the relative light signal variability. The constant (labelled B in preceding discussions) is equal to the slope of a plot of basis weight versus the logarithm of the average or DC transmitted light signal. The relationship is illustrated graphically in the plot of FIG. 5. The slope can be determined in a straightforward way in an off-line manner by measuring the average light transmission for a number of paper samples having known, different basis weights. If the slope is found to vary slightly with weight or with paper characteristics such as color or ash content, it is possible to find the slope of the basis weight versus the logarithm of the transmitted light signal appropriate to the paper type of interest.

As an alternative to this off-line calibration method for determining the relationship between the basis weight and the transmitted light signal, the calibration could also be carried out in an "on-line" manner in situations where a separate, additional basis weight sensor is present and is measuring basis weight on the same paper being viewed by the formation sensor of the current invention. In this case, the true basis weight value of the sheet being observed could be measured by the second basis weight sensor, while the DC transmitted light signal could be obtained from the basis weight formation sensor of the current invention. Combining basis weight and DC transmitted light signal values from the on-line sensors would then allow an on-line calibration of basis weight vs logarithm of transmitted light signal to be carried out in a straightforward way.

For either the on-line or off-line calibration methods just described, involving the determination of the slope of the basis weight vs the logarithm of DC sensor signal curve, it is not necessary to know or adjust the overall electronic gain of the DC signal component channel. This independence of the DC gain is due to the fact that it is the logarithm of the DC component which enters into the procedure, and overall multiplicative factors for the DC signal (which become additive factors when the logarithm is computed) cancel out in the calculation of the slope of the curve.

In a device constructed according to the present invention, the relative signal variation (AC signal component divided by DC component) of the transmitted signal is the major parameter in the formation calibration, not simply the absolute signal variation. This removes extraneous factors which would otherwise adversely affect the signal output. These factors include mechanical misalignment of the source lamp and the receiver light pipe, source lamp drifts in intensity, dirt buildup, etc. The relative signal variation can be determined in a precise way by using the presently preferred embodiment discussed above.

In addition, a device constructed in accordance with the present invention, such as the presently preferred embodiment discussed above, provides a paper manufacturer with output signals which correspond to three important parameters in paper manufacturing: (1) the magnitude of the local variations in the basis weight of the sheet caused by flocs of predetermined sizes or range of sizes; (2) the strength of the weakest portion or portions of the sheet; and (3) the size of the flocs forming the sheet. By monitoring these parameters, the paper manufacturer can adjust his or her paper making processes to provide a sheet of paper having evenly distributed fibers. Such a well-formed sheet will have high strength, good optical and textural properties and good printing quality.

One preferred embodiment of the basis weight formation sensor and signal processing circuitry has been described. Nevertheless, it will be understood that various modifications may be made to the sensor or signal processing circuitry described herein without departing from the spirit and scope of the invention. For example, where the diameter of the light pipe of the sensor corresponds to the smallest floc size which the paper manufacturer desires to examine, then the highest frequency component of the signal from the sensor will correspond to flocs having a minimum size equal to the diameter of the light pipe. Thus, a bandpass filter in the first channel is not necessary if one only wanted to examine signals from the first channel corresponding to flocs having a minimum size equal to the diameter of the light pipe. Instead, the amplified basis weight formation sensor signal can be fed directly to the RMS-AC to DC converter of the first channel.

Figure 5:
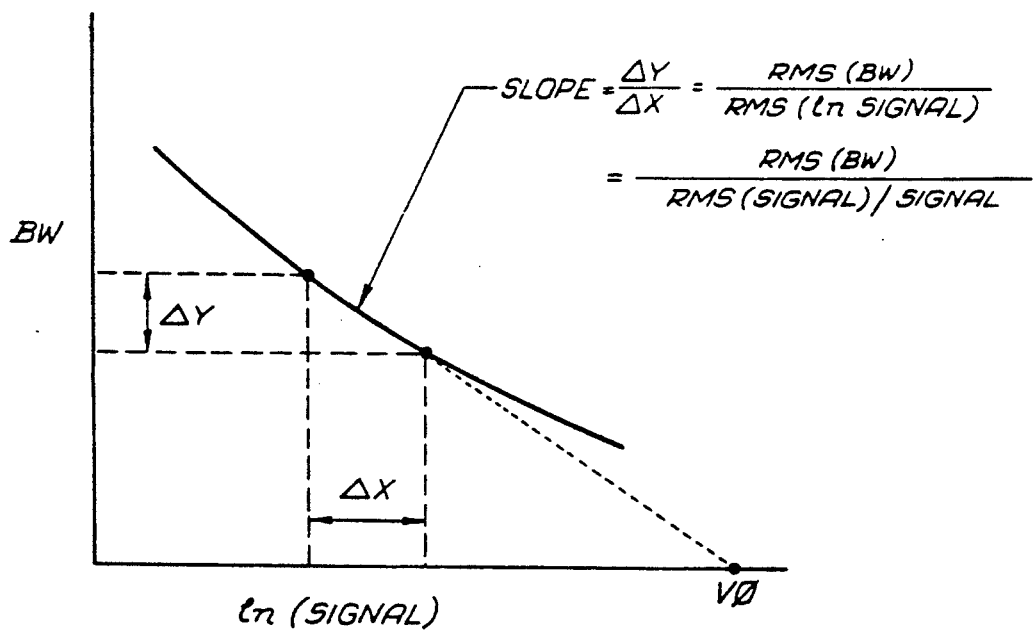
FIG. 5 illustrates the relationship between basis weight and the logarithm of the transmitted light signal.

One modification to the preferred embodiment is a technique for continuously updating the sensor calibration to maintain its accuracy under conditions of changing paper properties such as color or ash content. In this technique the assumption is made that small changes in the formation sensor calibration induced by small changes in the paper properties do not affect the value of the sensor signal evaluated at zero basis weight, V0 (V0 is defined by straight-line extrapolation of the portion of the calibration curve of interest to zero basis weight, as illustrated in FIG. 5). Since one point on the straight-line approximation to the calibration curve is thereby fixed, the slope of the straight line can be easily determined from a single additional point. In mathematical terms, the assumption is that small calibration changes do not affect the value of V0 in the following calibration equation:

$$BW = B*ln(V0) - B*ln(V)$$

(Here the calibration constant $B*ln(V0)$ replaces the constant A used in the initial discussion of this empirical calibration equation.) Thus, it is assumed that small calibration changes are reflected in the slope of the curve, B, and not in the intercept determined by V0. In an on-line situation, a second basis weight sensor can be used to provide values of the basis weight BW, while the formation sensor provides values of average formation sensor signal V. Here V may be corrected for overall signal level variations arising from source lamp drifts, dirt buildup, etc., by means of periodic off-sheet standardization. The readings from the formation sensor and from the second basis weight sensor can be combined via the above equation to generate a constantly updated value of the calibration constant B:

$$B = BW/[ln(V0) - ln(V)] = BW/[ln(V0/V)]$$

In practice, the basis weight BW and formation sensor signal V would be averaged over a suitable time interval to ensure accuracy of the updated value of B, while the constant V0 would be determined in the initial sensor calibration. In cases where the qualifying assumption above is not sufficiently valid to use this simple calibration updating technique, it is of course still possible to do on-line formation sensor calibration described previously by fitting several basis weight vs ln(signal) points in order to directly determine the slope of the curve, B.

Furthermore, the signal processing circuitry may be modified, if desired, such that the input to the peak detector and floc size measuring circuits can be selected from the bandpass filter of any desired channel. Moreover, sheet materials other than paper may be passed through the sensor and characterized by the device of the present invention. Thus, the present invention is not limited to the preferred embodiment described herein, nor is it limited strictly to use with paper.

What is claimed is:

1. A sheet formation characterizing device, comprising:
    formation sensor means for sensing the basis weight of a portion of a sheet of material and producing a basis weight signal indicative of the basis weight of the portion of the sheet;
    first circuit channel, said first circuit channel comprising at least one bandpass filter circuit containing a bandpass filter having an input for receiving the basis weight signal and a bandpass output signal comprising only those frequency components of the basis weight signal within a predetermined frequency range, the bandpass filter circuit further including an AC to DC converter for receiving the bandpass output signal and generating a DC output signal indicative of the root-mean-square value of the bandpass output signal;
    a second circuit channel, said second circuit channel having a voltage to frequency converter for generating an output signal indicative of the average value of the basis weight signal, and
    basis weight output means for determining the ratio of the DC output signal of the first circuit channel to the output signal of the second circuit channel and producing an output signal corresponding to variation in absolute basis weight values.

2. The device of claim 1, further comprising means for varying the cutoff frequency range of the bandpass filter directly with respect to the speed at which the sheet moves through the formation sensor means.

3. The device of claim 1 or claim 2, having a plurality of bandpass filter circuits, and wherein the frequency range passed by each bandpass filter circuit is different from the frequency range passed by any of the other bandpass filter circuits.

4. The device of claim 1, further comprising:
    peak detector means, operatively coupled to the formation sensor means, for generating a peak detector output signal indicative of the value of at least one peak in the basis weight signal received by the peak detector means during a predetermined time interval, the value of the peak in the basis weight signal being indicative of the lowest basis weight of the sheet sensed during the predetermined time interval.

5. The device of claim 1, further comprising:
    floc size measuring means, operatively coupled to the formation sensor means, for generating a floc size output signal indicative of the number of times the basis weight signal received by the floc size measuring means achieves a predetermined value during a predetermined time interval.

6. The device of claim 1, further comprising:
    calibration means for accurately determining the relative electronic gains of the first and second circuit channels and having a chopper wheel which modulates the basis weight signal.

7. A method of characterizing the formation of a sheet of material moving by a sensor in the machine-direction, comprising the steps of:
    sensing the basis weight of a portion of the sheet and producing a basis weight signal indicative of the basis weight of that portion of the sheet;
    filtering the basis weight signal to produce at least first and second channel signals, the first channel signal being produced by filtering the basis weight signal to remove variations in the basis weight signal above a first frequency and below a second frequency and the second channel signal being produced by filtering the basis weight signal to remove variations in the basis weight signal above a third frequency and below a fourth frequency;
    producing a first output signal indicative of the root-mean-square value of the first channel signal;
    producing a second output signal indicative of the root-mean-square value of the second channel signal;
    producing an averaged output signal indicative of the average value of the basis weight signal;
    producing a value proportional to the basis weight variations in the sheet having a frequency between the first and second frequencies by determining the ratio of the first output signal to the averaged output signal;
    producing a value proportional to the basis weight variations in the sheet having a frequency between the third and fourth frequencies by determining the ratio of the second output signal to the averaged output signal;
    measuring the speed of the sheet in the machine-direction and producing a signal indicative thereof; and
    adjusting the first, second, third, and fourth frequencies in accordance with the signal indicative of the speed of the sheet in the machine-direction so that each frequency corresponds with a predetermined floc size.

8. The method of claim 7 wherein the first, second, third, and fourth frequencies are proportional to the speed of the sheet in the machine-direction so that each frequency corresponds with a predetermined floc size.

9. The method of claim 7, wherein the second and third frequencies are approximately equal to value, whereby the formation of the sheet is characterized between the first and fourth frequency.

10. The method of claim 9, wherein the first frequency is approximately twice the value of the second frequency and the third frequency is approximately twice the value of the fourth frequency.

11. A method for calibrating a formation sensor which directs a light through a sheet and detects the portion of the light transmitted through the sheet to produce a signal indicative of variations in the basis weight so that the sensor expresses the variations in basis weight in true basis weight units, comprising the steps of:
    determining the basis weight of the sheet with a basis weight sensor;

directing the light through the sheet and detecting the average light transmission of the sheet with the formation sensor;

updating the value of the slope of a curve representing the basis weight versus the logarithm of the average light transmission; and multiplying the signal of the formation sensor by the slope.

12. The method of claim 11, wherein the basis weight sensor is a beta-ray sensor.

13. The method of claim 11, wherein the slope of the curve is represented by the formula:

$$B/ = BW/[ln(VO/V)]$$

wherein
B = the slope of the curve;
BW = the basis weight of the sheet;
VO = the average signal of the formation sensor when the basis weight of the sheet is zero; and
V = the average signal of the formation sensor.

* * * * *